(12) United States Patent
De Cola et al.

(10) Patent No.: US 9,012,038 B2
(45) Date of Patent: Apr. 21, 2015

(54) PHOSPHORESCENT METAL COMPLEX COMPOUND, METHOD FOR THE PREPARATION THEREOF AND RADIATING COMPONENT

(75) Inventors: Luisa De Cola, Münster (DE); David Hartmann, Erlangen (DE); Wiebke Sarfert, Herzogenaurach (DE); Günter Schmid, Hemhofen (DE)

(73) Assignee: Osram GmbH, Munich (DE)

( * ) Notice: Subject to any disclaimer, the term of this patent is extended or adjusted under 35 U.S.C. 154(b) by 1041 days.

(21) Appl. No.: 12/737,466

(22) PCT Filed: Jul. 15, 2009

(86) PCT No.: PCT/EP2009/059092
§ 371 (c)(1),
(2), (4) Date: Apr. 13, 2011

(87) PCT Pub. No.: WO2010/007107
PCT Pub. Date: Jan. 21, 2010

(65) Prior Publication Data
US 2011/0187265 A1    Aug. 4, 2011

(30) Foreign Application Priority Data
Jul. 18, 2008    (DE) .......................... 10 2008 033 929

(51) Int. Cl.
| | | |
|---|---|---|
| H05B 33/14 | (2006.01) |
| H01L 51/54 | (2006.01) |
| C09K 11/06 | (2006.01) |
| H01L 51/00 | (2006.01) |
| C07F 15/00 | (2006.01) |
| H01L 51/50 | (2006.01) |

(52) U.S. Cl.
CPC .......... *H01L 51/009* (2013.01); *C07F 15/0033* (2013.01); *C09K 11/06* (2013.01); *H01L 51/0085* (2013.01); *H01L 51/0086* (2013.01); *H05B 33/14* (2013.01); *C09K 2211/1007* (2013.01); *C09K 2211/1029* (2013.01); *C09K 2211/1059* (2013.01); *C09K 2211/185* (2013.01); *H01L 51/5032* (2013.01); *Y10S 428/917* (2013.01)

(58) Field of Classification Search
None
See application file for complete search history.

(56) References Cited

U.S. PATENT DOCUMENTS

| | | | |
|---|---|---|---|
| 190,359 A | 5/1877 | Peet | |
| 6,830,828 B2 | 12/2004 | Thompson et al. | |
| 6,902,830 B2 | 6/2005 | Thompson et al. | |
| 7,001,536 B2 | 2/2006 | Thompson et al. | |
| 2006/0286404 A1 | 12/2006 | Wu | |
| 2007/0001166 A1 | 1/2007 | Tao et al. | |
| 2007/0141394 A1 | 6/2007 | Cheng et al. | |
| 2007/0190359 A1 | 8/2007 | Knowles et al. | |
| 2008/0038586 A1 | 2/2008 | Nishizeki et al. | |
| 2008/0161568 A1 | 7/2008 | Chi et al. | |
| 2009/0096353 A1 | 4/2009 | Takahashi et al. | |
| 2009/0239000 A1* | 9/2009 | Sugita et al. .................. 428/1.1 |
| 2010/0044637 A1 | 2/2010 | Nazeeruddin et al. | |

FOREIGN PATENT DOCUMENTS

| | | |
|---|---|---|
| EP | 1 692 244 | 4/2007 |
| EP | 1 486 552 | 12/2007 |
| EP | 1 904 508 | 4/2008 |
| EP | 1953843 | 8/2008 |
| EP | 2275428 | 1/2011 |
| JP | 2003-208982 | 7/2003 |
| JP | 2007-504272 | 3/2007 |
| JP | 2007-137872 | 6/2007 |
| JP | 2007-169541 | 7/2007 |
| JP | 2008-504342 | 2/2008 |
| WO | 03/018653 | 3/2003 |
| WO | 2004/101707 | 11/2004 |
| WO | 2005/019373 | 3/2005 |
| WO | 2005/097942 | 10/2005 |
| WO | 2005/097943 | 10/2005 |
| WO | 2006/000544 | 1/2006 |
| WO | 2006/008976 | 1/2006 |
| WO | 2006/013738 | 2/2006 |
| WO | 2006/024997 | 3/2006 |
| WO | 2006/098120 | 9/2006 |
| WO | 2006/135076 | 12/2006 |
| WO | 2007/052431 | 5/2007 |
| WO | 2007/095118 | 8/2007 |
| WO | 2007/004113 | 11/2007 |
| WO | 2009/000673 | 12/2008 |

OTHER PUBLICATIONS

English language of Japanese Office Action for related Japanese Patent Application No. 2011-517921, mailed May 7, 2013, 11 pages.
Stepan Chuprakov et al., "Direct PD-Catalyzed Arylation of 1,2,3-Triazoles," Organic Letters, 2007, vol. 9, No. 12, pp. 2333-2336.
Duan Liu, "Triazole-Based Monophosphines for Suzuki-Miyaura Coupling and Amination Reactions of Aryl Chlorides," Organic Letters, 2005, vol. 7, No. 22, pp. 4907-4910.
David Amantini et al., "Synthesis of 4-Aryl-1H-1,2,3-triazoles through TBAF-Catalyzed [3+2] Cycloaddition of 2-Aryl-1-nitroethenes with TMSN$_3$ under Solvent-Free Conditions," Journal of Organic Chemistry, 2005, 70, pp. 6526-6529.
Karine Barrel et al., "Efficient Conversion of Aromatic Amines into Azides: A One-Pot Synthesis of Triazole Linkages," Organic Letters, 2007, vol. 9, No. 9, pp. 1809-1811.

(Continued)

*Primary Examiner* — Marie R. Yamnitzky
(74) *Attorney, Agent, or Firm* — Staas & Halsey LLP

(57) ABSTRACT

A phosphorescent metal complex compound, a method for the preparation thereof and a radiation component, in particular an organic light emitting electrochemical cell (OLEEC) use a bidentate ligand containing a triazole unit. Some of the blue emitters shown here for the first time, in particular the class of iridium complex compounds presented here, are the bluest emitters that have ever existed.

7 Claims, 9 Drawing Sheets

(56) References Cited

OTHER PUBLICATIONS

D. R. Rogue et al., "Synthesis of 1,2,3-Triazoles by Cycloadditions of Azides with Enol Ethers," Synthesis, 2005, No. 15, pp. 2497-2502.
Y. M. Wu et al., "Regiospecific Synthesis of 1,4,5-Trisubstituted-1,2,3-triazole via One-Pot Reaction Promoted by Copper(I) Salt," Synthesis, 2005, No. 8, pp. 1314-1318.
Vsevolod V. Rostovtsev et al., "A Stepwise Huisgen Cycloaddition Process: Copper(I)-Catalyzed Regioselective 'Ligation' of Azides and Terminal Alkynes**," Angew. Chem. Int. Ed. 2002, 41, No. 14, pp. 2596-2599.
José Barluenga et al., "Developments in Pd Catalysis: Synthesis of 1$H$-1,2,3-Triazoles from Sodium Azide and Alkenyl Bromides," Angew. Chem. Int. Ed., 2006, 6893-6896.
Enrico Orselli, "Blue-Emitting Iridium Complexes with Substituted 1,2,4-Triazole Ligands: Synthesis, Photophysics, and Devices," Inorganic Chemistry, vol. 46, No. 26, 2007, pp. 11082-11093.
Bedri Mehmetaj, "Synthesis, Characterization, X-ray Crystal Structure, Redox and Photophysical Properties of Polypyridylruthenuim(II) Complexes Containing Carboxylate-Substituted Pyridyltriazoles," Eur. J. Inorg. Chem., 2002, 1765-1771.
Luisa De Cola, "Electronic energy transfer in bimetallic Ru-Os complexes containing the 3,5-bis (pyridine-2-yl)-1, 2,4-triazolate bridging ligand," Chemical Physics Letters, vol. 178, No. 5,6, Apr. 5, 1991, pp. 491-496.
John H. van Diemen et al., "Electrochemical and Photophysical Properties of New Triazole-Bridged Heterobimetallic Ruthenium—Rhodium and Ruthenium—Iridium Complexes," Inorg. Chem., 1992, 31, pp. 3518-3522.
Ronald Hage et al., "Homo- and Heteronuclear Ruthenium and Osmium Complexes Containing an Asymmetric Pyrazine-Based Bridging Ligand," Inorg. Chem., 1997, vol. 36, No. 14, 7 pp. 3139-31457.
Chris Richardson et al., "4,5-Di(2-pyridyl)-1,2,3-triazolate: the elusive member of a family of bridging ligands that facilitate strong metal-metal interactions," Dalton Transactions, 2008, pp. 2534-2537.
Makoto Obata et al., "Syntheses, structural characterization and photophysical properties of 4-(2-pyridyl)-1,2,3-triazole rhenium(I) complexes," Dalton Transactions, 2008, pp. 3292-3300.
Bruce H. Lipshutz et al., "Heterogenous Copper-in-Charcoal-Catalyzed Click Chemistry," Angew. Chem. Int. Ed., 2006, 45, pp. 8235-8238.
Ze-Yi Yan et al., "General synthesis of (1-substituted-1$H$-1,2,3-triazol-4-ylmethyl)-dialkylamines via a copper(I)-catalyzed three-component reaction in water," Tetrahedron 61, 2005, pp. 9331-9337.
Shin Kamijo et al., "Synthesis of Triazoles from Nonactivated Terminal Alkynes via the Three-Component Coupling Reaction Using a Pd(0)—Cu(I) Bimetallic Catalyst," J. Am. Chem. Soc. 2003, 125, pp. 7786-7787.
Sergey Lamansky et al., "Synthesis and Characterization of Phosphorescent Cyclometalated Iridium Complexes," Inorganic Chemistry, 2001, vol. 40, No. 7, Abstract Only.
International Search Report for PCT/EP2009/059092, mailed Oct. 27, 2009.
Chen et al., "Blue Phosphorescent Heteroleptic Triscyclometallated Ir (III) Organometallic Complexes," 22$^{nd}$ International Conference on Organometallic Chemistry (ICOMC 2006) Book of Abstracts, Poster Presentations, Zaragoza, Jul. 23-28, 2006, vol. 2, Jul. 23, 2006, p. 662, document included.
Jason D. Slinker et al., "Direct measurement of the electric-field distribution in a light-emitting electrochemical cell," Nature Materials, vol. 6, Nov. 2007, pp. 894-899.
Qibing Pei et al., "Polymer Light-Emitting Electrochemical Cells," Science, vol. 269, Aug. 25, 1995, pp. 1086-1088.

* cited by examiner

1-H-NMR

31-P-NMR

1-H-NMR

PHOSPHORESCENT METAL COMPLEX COMPOUND, METHOD FOR THE PREPARATION THEREOF AND RADIATING COMPONENT

CROSS REFERENCE TO RELATED APPLICATIONS

This application is based on and hereby claims priority to International Application No. PCT/EP2009/059092 filed on Jul. 15, 2009 and German Application No. 10 2008 033 929.6 filed on Jul. 18, 2008, the contents of which are hereby incorporated by reference.

BACKGROUND

The invention relates to a phosphorescent metal complex compound, a method for preparing same and a radiation emitting component, in particular an organic light emitting electrochemical cell (OLEEC).

Organic electroluminescent elements generally have at least one organic layer which is sandwiched between two electrodes. As soon as voltage is applied to the electrodes, electrons are injected from the cathode into the lowest unoccupied molecular orbitals of the organic light emitting layer and migrate to the anode. Correspondingly, holes are injected from the anode into the highest occupied molecular orbitals of the organic layer and migrate accordingly to the cathode. In the cases where migrating hole and migrating electron come together within the organic light emitting layer on a light emitting material, an exciton is produced which decays with the emission of light. In order that light can exit the electroluminescent element at all, at least one electrode must be transparent, in most cases said one electrode being of indium tin oxide which is used as the anode. The ITO layer is normally deposited on a glass substrate.

In the organic light emitting diodes (OLEDs), particularly in the case of the OLEDs based on small molecules, a so-called multilayer structure is implemented, because, in addition to the light emitting layer, efficiency-increasing layers such as hole and/or electron injection layers are disposed between the electrodes for better transference of the charge carriers. Highly reactive materials are often used here, which means that, among other things, encapsulation is critical for the service life of the light emitting element, as it protects the auxiliary layers from decomposition.

Alternatively, there are the so-called organic light emitting electrochemical cells (OLEECs) which are of simpler design than the OLEDs and which in most cases can be implemented by simply mounting an organic layer between two electrodes and subsequent encapsulation. The active layer of an OLEEC is generally made of a material which is a mixture of an ion conductor/electrolyte or also of a completely inert matrix (isolator) with an emitting species. Suitable for this purpose are ionic transition metal complexes (iTMC for short) such as ruthenium trisbipyridine hexafluorophosphates in polymer matrices. However, there is as yet an inadequate selection of suitable materials, there being in particular a dearth of blue emitting materials.

SUMMARY

One potential object is therefore to create a material class suitable for use in OLEEC cells and to specify a synthesis to that end. A further potential object is to specify an OLEEC cell constructed using the material class and the use of said material class in OLEEC cells.

The inventors propose a phosphorescent metal complex compound comprising at least one metallic central atom M and at least one ligand coordinated by the metallic central atom and containing a bidentate ligand with a triazole unit. The inventors also propose a radiation emitting component comprising a substrate, a first electrode layer on said substrate, at least one organic emitting layer on the first electrode layer and a second electrode layer on the organic emitting layer, wherein the organic emitting layer comprises a phosphorescent metal complex compound. The inventors further propose a method for preparing a phosphorescent metal complex compound, comprising the following A) Preparing a central atom compound of a metallic central atom, having exchange ligands coordinated to the central atom, B) Mixing the central atom compound and a ligand dissolved in a first solvent to form the metal complex compound, the exchange ligand being replaced by the ligand which is coordinated in a bidentate manner to the central atom and comprises a triazole unit.

In particular, the material class is that of a metal complex having the following general structure I:

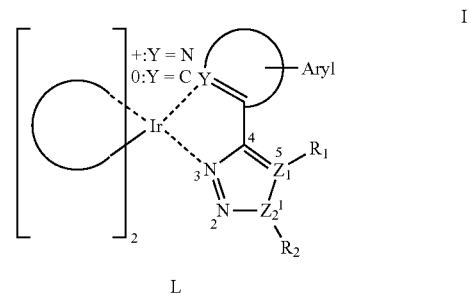

L

Said complex has two known ligands L (shown on the left) which can be selected independently of one another and can be the same or different and preferably complex in a bidentate manner, in particular via a carbon and a nitrogen atom, said known ligands L being, for example, according to one embodiment, the conventional and also commercially available emitters with phenylpyridine ligands, substituted e.g. with fluorine for blueshifting. Known complexes with iridium as the central atom are 2,4-difluorophenyl-2-pyridyl-iridium(III) picolinate (FIrPic) or $FIr_6$.

According to another embodiment of the material class, the two ligands L shown to the left of the metal atom and already known in the literature are preferably selected from the following documents: WO 2005/097942 A1, WO 2006/013738 A1, WO 2006/098120A1, WO 2006/008976 A1, WO 2005/097943 A1, U.S. Pat. No. 6,902,830, U.S. Pat. No. 7,001,536, U.S. Pat. No. 6,830,828, WO 2007/095118 A2, US 2007 0 190 359 A1 (UDC), EP 1 486 552 B1, for example, 2-phenylpyridine or 2-phenylimidazole as well as related and similar structures such as phenanthridine shall be mentioned by way of example.

According to another advantageous embodiment, the two known ligands L can have, for example, carbene functionality which is used as a deep blue emission source. Examples of said ligands L may be found in the publications WO 2005/19373 or EP 1 692 244 B1.

Further examples of possible ligands L are disclosed in the publications EP 1 904 508 A2, WO 2007/004113 A2, WO 2007/004113 R4A3, said ligands L also being shown in the context of charged metal complexes having at least one phenylpyridine ligand with corresponding donor groups such as dimethylamino. The compounds exhibit an increased LUMO level of the complex, acceptor groups such as 2,4 difluoro being introduced into the phenyl ring in order to lower the level of the HOMO orbital. It is shown that by varying the ligands and their substituents, the emission color can be varied across the entire visible spectrum.

In addition to the ligands L, the metal complex according to the structural formula I has at least one triazole ligand, either a 1,2,3- or a 1,2,4-triazole. The triazole unit has a heteroaromatic or an aromatic substituent in ortho position with respect to the two mutually adjacent nitrogens of the triazole ring, resulting in a structure of the general formula I.

The 1,2,3-triazole compounds are obtained with $Z_2$=N and $Z_1$=C whereas the 1,2,4-triazole compounds are produced with $Z_2$=C and $Z_1$=N. The ring numbering system was developed on the basis of the 1,2,3-triazoles and, for the purposes of this description, is used as shown, the 1,2,4-triazoles of course being obtained from the 1,2,3-triazoles by exchanging the C and N substituents Z. In both cases, the carbon atom with the substituent which causes the bidenticity of the entire ligand and which is preferably an aryl substituent, is numbered 4.

Preferably M=iridium. Also possible, however, are metals such as Re, Ru, Rh, Os, Pd, Pt, Au, Hg and Cu. The stoichiometry of the corresponding complexes will then vary depending on the coordination sphere of the respective central atom, in particular because not all metals form octahedral complexes like iridium.

Y is preferably nitrogen. This means that the hetero triazole ligands are neutral with respect to the inner coordination sphere. Charged substituents or substituents which can stabilize charge, i.e. are "chargeable", can be placed in the outer positions. The heteroaromatic ring contains, in the ortho position with respect to the bridge carbon atom, a nitrogen atom which, along with the nitrogen atom 2 in the triazole unit, is the second chelating atom of the ligand. For the case that Y=C, the conventional cyclometalated compound is produced, the triazole ligand being technically negatively charged.

This means that, for the case M=Ir, neutral species are obtained. Optionally, both aromatic units can still be linked via a second bridge.

According to another embodiment of the material class, $R_1$ and/or $R_2$ are linked to other residues $R_1'$ and/or $R_2'$ of another metal complex. The linking group can be taken from the examples given below. If more highly functional links are selected, more highly crosslinked complexes right up to polymer complexes are accessible. On the other side, a bridge can be formed via one of the known ligands L to one or more further complexes with ligands and central atoms. Access to oligomeric and polymeric compounds is also possible via this side. M can also be Re, Os, Pt, Au, Hg as well as Ru, Rh, Pd and Ag, Cu. Moreover, $R_1$ and/or $R_2$ may additionally be coordinated to M. Another alternative is that at least two metallic central atoms M are coordinated to one another via a metal-metal interaction.

For the case that Y and $Z_1$ are both N, the following structure Ia is produced

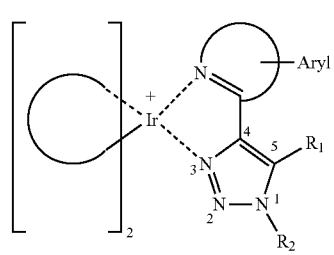

Ia

The proposed metal complex compound preferably comprises a group of the structural formula II

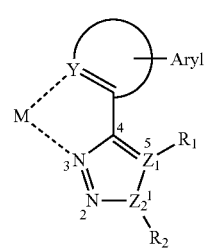

II where

M=Ir, Re, Os, Pt, Au, Hg, Ru, Rh, Pd, Ag, Cu

Y, Z=N or C

R=independently of one another —H, branched alkyl residues, unbranched alkyl residues, condensed alkyl residues, cyclic alkyl residues, completely or partially substituted unbranched alkyl residues, completely or partially substituted branched alkyl residues, completely or partially substituted condensed alkyl residues, completely or partially substituted cyclic alkyl residues, alkoxy groups, amines, amides, esters, carbonates, aromatics, completely or partially substituted aromatics, heteroaromatics, condensed aromatics, completely or partially substituted condensed aromatics, heterocyclics, completely or partially substituted heterocyclics, condensed heterocyclics, halogens, pseudohalogens and Aryl=any partially or completely substituted aromatic or heteroaromatic residue which can also be condensed, can establish a bridge to another compound, and/or can be present in condensed form or fused with other aromatics or heteroaromatics, and linked to other cyclic compounds.

Some examples will now be given of the ring structure of the heteroaromatics in the ortho position with respect to the two adjacent nitrogens of the triazole ring, e.g. a 6-membered ring. In the simplest case, this is a pyridine ring or a derivative thereof:

whereas

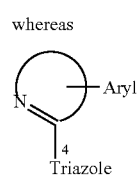

Triazole

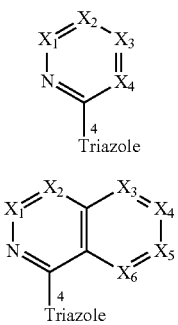

a

Triazole

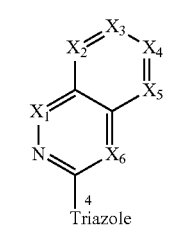

b

Triazole

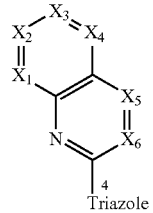

c

Triazole d

Triazole

X means either the residue —C—R, where R is one of the substituents listed below or a nitrogen atom with a free electron pair.

Examples of the substituents "a" on the triazole are:

Pyridine derivatives, where $X_1$, $X_2$, $X_3$, $X_4$ are all —C—R residues, all the R being independent of one another and one of the substituents listed below.

Pyrimidine derivatives, where $X_2$=N or $X_4$=N, all the other residues being —C—R.

Pyrazine derivatives, where $X_3$=N, all the others being —C—R.

Pyridazine derivatives, where $X_1$=N, all the others being —C—R.

1,3,5-triazine derivatives, where $X_2$=N and $X_4$=N, all the others being —C—R.

Examples of the substituents "b" on the triazole are:

Isoquinoline derivatives, where all the X are the residues —C—R with a linkage to the triazole ligand in position 1.

Quinazoline derivatives, where $X_2$=N, and all the other residues are of type —C—R.

Phthalazine derivatives, where $X_1$=N, and all the other residues are of type —C—R.

Examples of the substituents "c" on the triazole are:

Isoquinoline derivatives which are structural isomers of the isoquinoline derivatives of the abovementioned derivatives for the substituents "b" on triazole.

Examples of the substituents "d" on the triazole are:

Quinoline derivatives, where all the X are residues of type —C—R.

Quinoxaline derivatives, where $X_5$=N and all the others are of type —C—R,

Quinazoline derivatives with $X_6$=N and all the other residues are of type —C—R.

More highly condensed systems can be prepared in a similar manner, e.g. pteridine, acridine, phenazine, phenanthridine and/or purine and derivatives thereof as well as compounds with additional heteroatoms such as oxygen or sulfur in the condensed ring which carries the coordinating nitrogen atom.

A number of examples will now be given of the ring structure of the heteroaromatic in the ortho position with respect to the two adjacent nitrogens of the triazole ring, e.g. a 5-membered ring:

In the simplest case, the 6-membered ring is a pyridine ring. Examples of hetero five-ring substituted triazoles are given here:

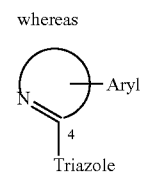

whereas

Triazole

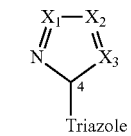

a

Triazole

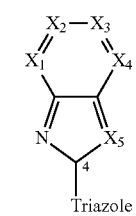

b

Triazole

Examples of the substituents "a" on the triazole are:

Oxazole derivatives, where $X_3$=O or $X_2$=O, and all the other residues are of type —C—R;

Thiazole derivatives, where $X_3$=S or $X_2$=S, and all the other residues are of type —C—R.

Isoxazole derivatives, where $X_1$=O and all the other residues are of type —C—R.

Isothiazole derivatives, where $X_1$=S, and all the other residues are of type —C—R.

Imidazole derivatives, where $X_1$, $X_2$ are residues of type —C—R and $X_3$ is a residue of type N—R.

Pyrazole derivatives, where $X_2$, $X_3$ are residues of type C—R and $X_1$ is a residue of type N—R.

Tetrazole derivatives, where $X_1$, $X_2$, $X_3$ all =N.

Examples of the substituents "b" on the triazole are:

Benzimidazole derivatives, where $X_5$ is of type N—R and $X_1$, $X_2$, $X_3$, $X_4$ are residues of type —C—R. Further nitrogen atoms may be contained in the linked benzene ring, thus producing benzimidazole analogs pyridine, pyrimidine, pyrazine or pyridazine ring, by substitution of the C—R by nitrogen.

Examples are purine derivatives: $X_5$ is a residue of type N—R and $X_1$, $X_3$, are of type N and $X_4$ are of type —C—R.

All the substituents R can be, independently of one another, H, methyl, ethyl or generally linear or branched, condensed (decahydronaphthyl, adamantyl), cyclic (cyclohexyl) or completely or partially substituted alkyl residues (C1-C20). The alkyl groups can be functional groups such as ether (ethoxy, methoxy, etc.), ester, amide, carbonates, etc. or halogens, preferably F. R is not limited to residues of the alkyl type, but can have substituted or unsubstituted aromatic systems such as phenyl, biphenyl, naphthyl, phenanthryl, etc. and benzyl, etc.

A summary of basic aromatic systems is shown in the Table below.

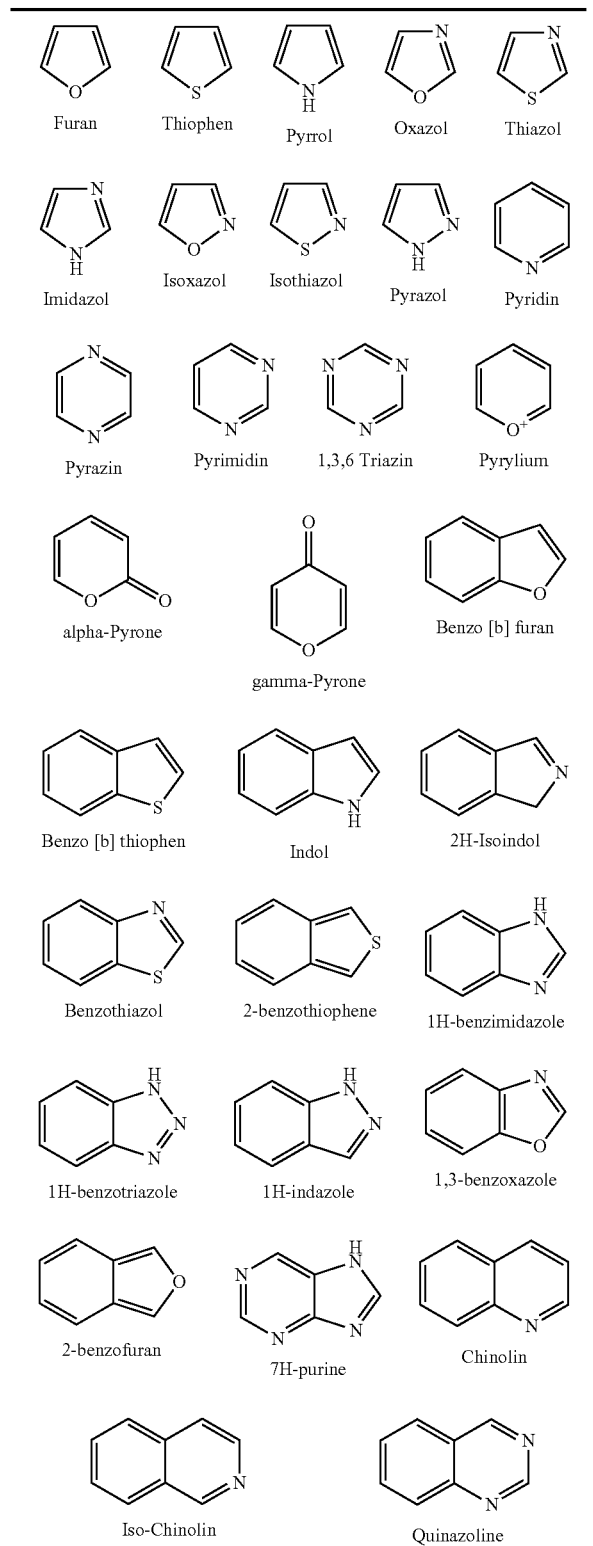

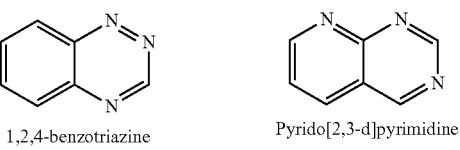

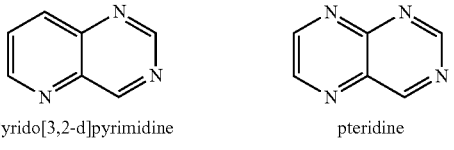

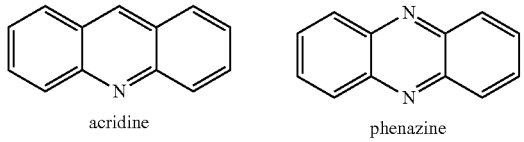

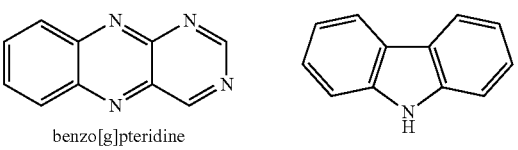

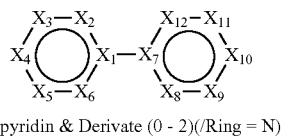

Bipyridin & Derivate (0 - 2)(/Ring = N)

Only the basic structures are shown here for simplicity's sake. Substitutions can occur here at any position with a potential bond valence.

Equally, the residue R can be of an organometallic nature, e.g. ferrocenyl, phtalacyaninyl or metal cations, e.g. surrounded by a functionalized crown ether, as shown below.

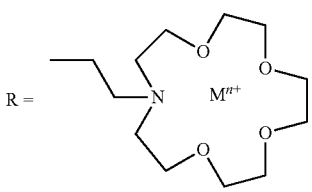 [SMILES: CCCN1CCOCCOCCOCCOCC1]

Lastly, the residue R can also be charged and therefore either bring charge into a hitherto uncharged complex, which is advantageous for OLEEC applications, or neutralize a charged complex and therefore make it accessible for OLED applications.

Examples of charged residues R are:

R =

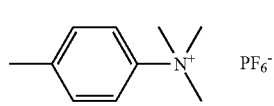

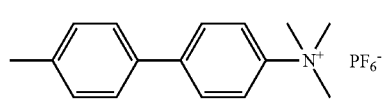

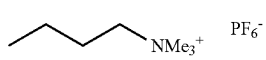

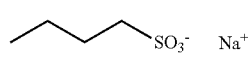

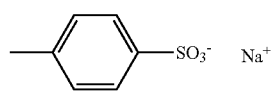

For synthesis of the 1,2,3-triazoles, there are various approaches, a number of which will be taken here via excerpts relating to the subject matter of the present description:

Synthesis Example 1

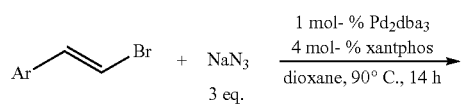

The palladium-catalyzed synthesis of 1H-triazole from alkenyl halogens and sodium azide is a completely new reaction in the context of palladium chemistry. See J. Barluenga, C. Valdés, G. Beltrán, M. Escribano, F. Aznar, Angew. Chem. Int. Ed., 2006, 45, 6893-6896.

Synthesis Example 2

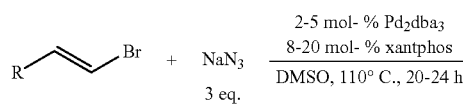

R: alkyl, vinyl

J. Barluenga, C. Valdés, G. Beltrán, M. Escribano, F. Aznar, Angew. Chem. Int. Ed., 2006, 45, 6893-6896.

Synthesis Example 3

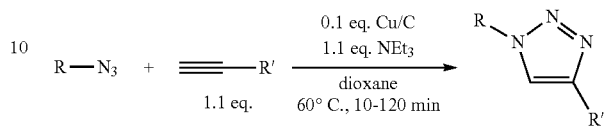

This is a highly efficient chemistry between azides and terminal alkynes, and can be heterogeneously catalyzed by copper nanoparticles on special charcoal. The reaction can be accelerated by the stoichiometric addition of $Et_3N$, by increasing the temperature or using microwave irradiation.

B. H. Lipshutz, B. R. Taft, Angew. Chem. Int. Ed., 2006, 45, 8235-8238.

Synthesis Example 4

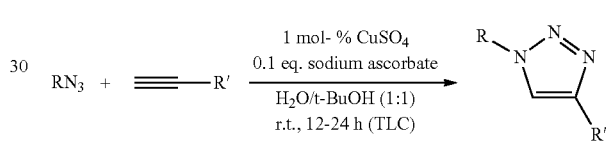

The copper-catalyzed stepwise cycloaddition of azides to terminal alkynes opens up a wide spectrum and enables 1,4-disubstituted-1,2,3-triazoles to be prepared in high yields and with high regioselectivity.

V. V. Rostovtsev, L. G. Green, V. V. Fokin, K. B. Sharpless, Angew. Chem., 2002, 114, 2708-2711.

Synthesis Example 5

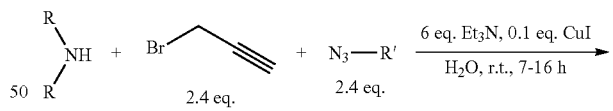

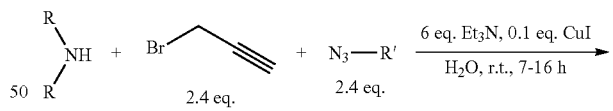

R: Alkyl
R': Ar, alkyl, benzyl

A copper(I)-catalyzed three-component reaction of amines with propargyl halides and azides in water produces 1-substituted-1H-1,2,3-triazol-4-ylmethyl)-dialkylamines. A synthetic advantage aside from the high selectivity is the low environmental impact, wide substrate scope as well as mild reaction conditions and good yields.

Z.-Y. Yan, Y.-B. Zhao, M.-J. Fan, W.-M. Liu, Y.-M. Liang, Tetrahedron, 2005, 61, 9331-9337.

Synthesis Example 6

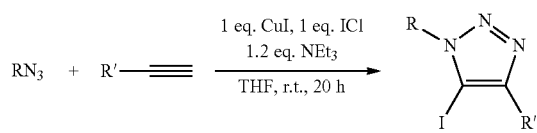

This is a method for the regiospecific synthesis of 1,4,5-trisubstituted-1,2,3-triazole which is catalyzed by copper(I) iodide. This is the first example of regiospecific synthesis of 5-iodo-1,4-disubstituted-1,2,3-triazole, which can be further elaborated to produce 1,4,5-trisubstituted-1,2,3-triazole derivatives.

Y.-M. Wu, J. Deng, Y. L. Li, Q.-Y. Chen, Synthesis, 2005, 1314-1318.

Synthesis Example 7

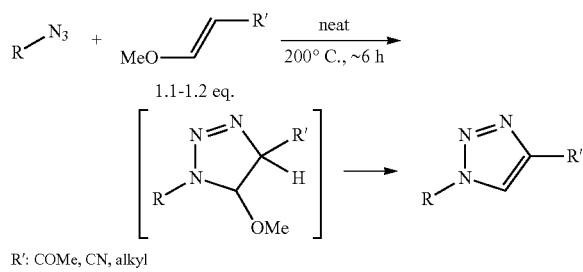

R': COMe, CN, alkyl 1,2,3-triazoles were prepared in moderate to good yields by cycloaddition of alkyl azides onto enol ethers under solventless conditions. This reaction can provide access to ring-fused triazoles that are unavailable by azide-alkyne cycloadditions. Moreover, the reaction can be easily scaled up from lab scale. The 1,2,3-triazoles thus produced can be readily derivatized.

D. R. Rogue, J. L. Neill, J. W. Antoon, E. P. Stevens, Synthesis, 2005, 2497-2502.

Synthesis Example 8

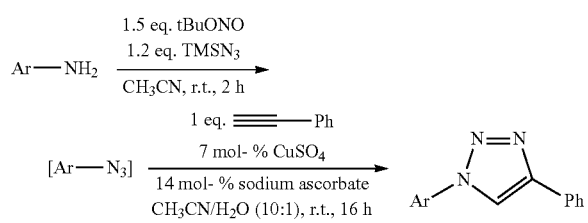

The synthesis of aromatic azides from the corresponding amines is accomplished under mild conditions with tert-butyl nitrite and azidotrimethylsilane. 1,4-disubstituted-1,2,3-triazoles were obtained in excellent yields from various aromatic amines without the need for isolation of the azide intermediates.

K. Barral, A. D. Moorhouse, J. E. Moses, Org. Lett., 2007, 9, 1809-1811.

Synthesis Example 9

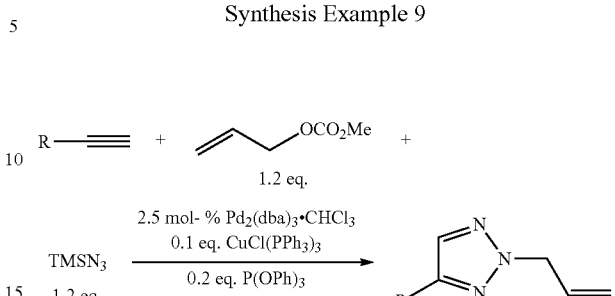

Triazoles were synthesized via a three-component coupling reaction with an unactivated terminal alkyne, an allyl carbonate, and a trimethylsilyl azide under palladium(0) and copper(I) bimetallic catalysis. The deallylation of the resulting allyltriazoles is also described.

S. Kamijo, T. Jin, Z. Huo, Y. Yamamoto, J. Am. Chem. Soc., 2003, 125, 7786-7787.

Synthesis Example 10

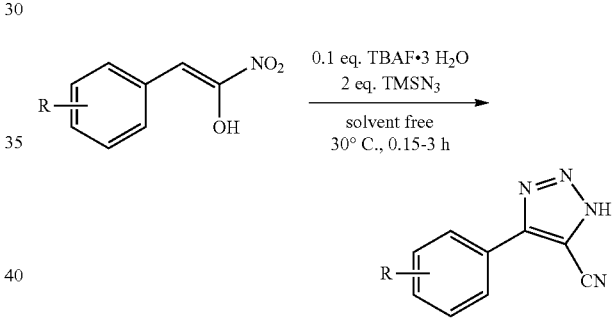

This involves TBAF-catalyzed [3+2] cycloaddition of 2-aryl-1-cyano- or 2-aryl-1-carbethoxy-1-nitroethenes with TMSN$_3$ under solvent-free conditions (SFC) which allows the preparation of 4-aryl-5-cyano- or 4-aryl-5-carbethoxy-1H-1,2,3-triazoles under mild reaction conditions with good to excellent yields.

D. Amantini, F. Fringuelli, O. Piermatti, F. Pizzo, E. Zunino, L. Vaccaro, J. Org. Chem., 2005, 70, 6526-6529.

Or:

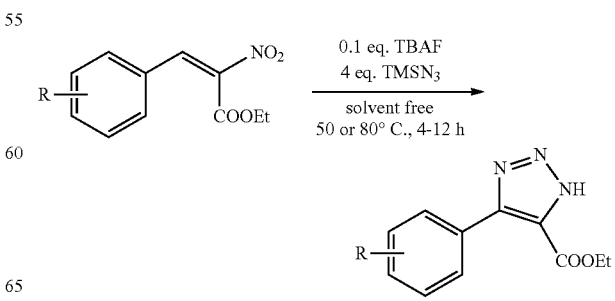

D. Amantini, F. Fringuelli, O. Piermatti, F. Pizzo, E. Zunino, L. Vaccaro, J. Org. Chem., 2005, 70, 6526-6529.

Synthesis Example 11

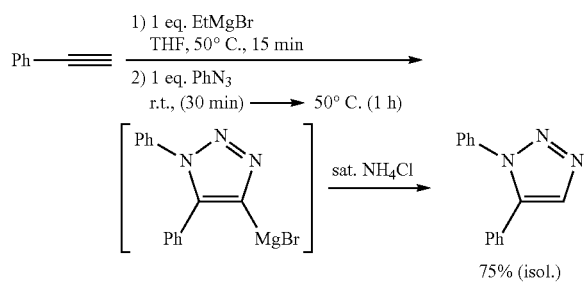

Triazole-based monophosphine ligands were prepared via efficient cycloadditions.

Palladium complexes derived therefrom are highly active catalysts for the Suzuki-Miyaura coupling reaction and amination reactions of aryl chlorides.

D. Liu, W. Gao, Q. Dai, X. Zhang, Org. Lett., 2005, 7, 4907-4910.

Synthesis Example 12

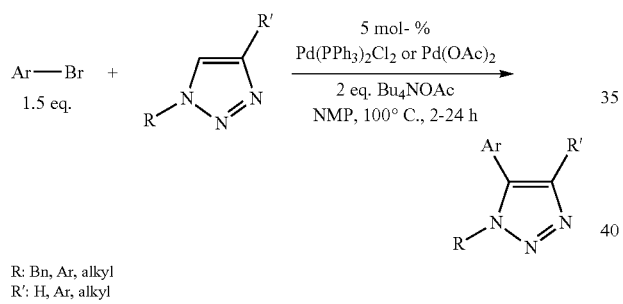

R: Bn, Ar, alkyl
R': H, Ar, alkyl

A highly efficient method for the synthesis of multisubstituted 1,2,3-triazoles via a direct palladium-catalyzed C-5 arylation reaction is presented.

S. Chuprakov, N. Chernyak, A. S. Dudnik, V. Gevorgyan, Org. Lett., 2007, 9, 2333-2336.

BRIEF DESCRIPTION OF THE DRAWINGS

These and other objects and advantages of the present invention will become more apparent and more readily appreciated from the following description of the preferred embodiments, taken in conjunction with the accompanying drawings of which.

DETAILED DESCRIPTION OF THE PREFERRED EMBODIMENT

Figure 1:
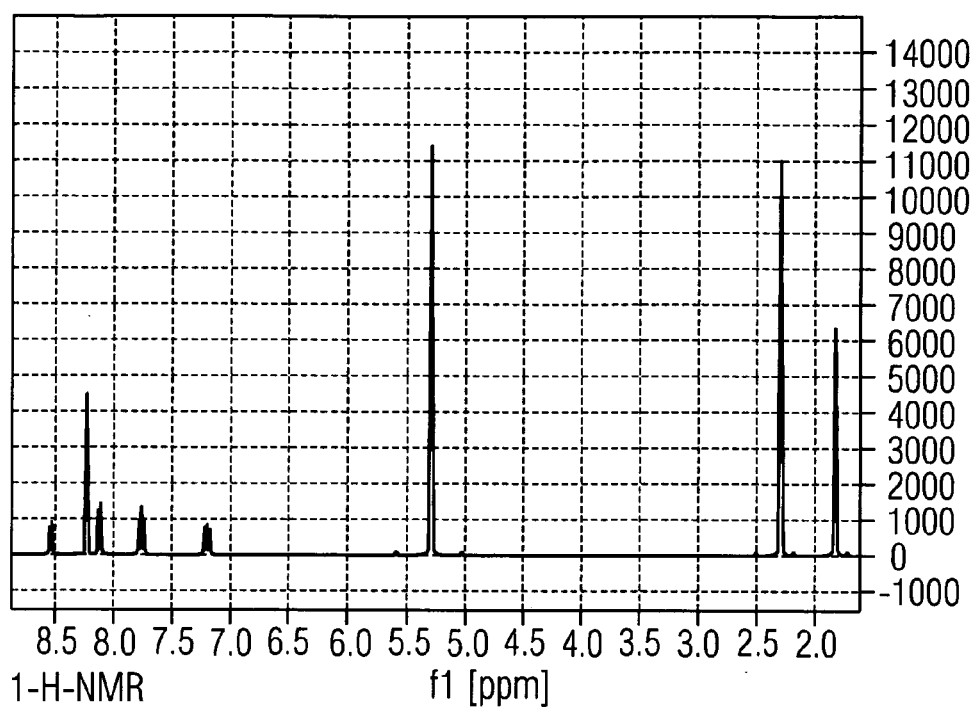
FIG. 1 shows the $^1$H proton spectrum of the compound.
Figure 2:
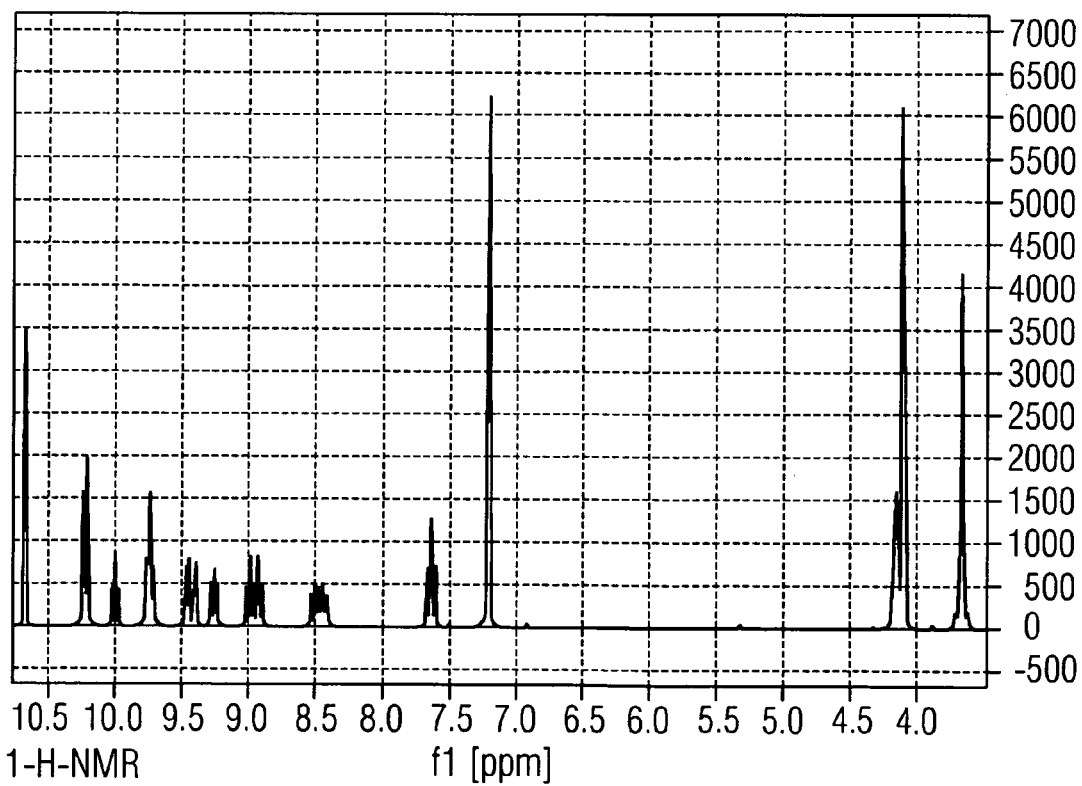
FIGS. 2 to 5 show the respective NMR spectra of the compound.
Figure 3:
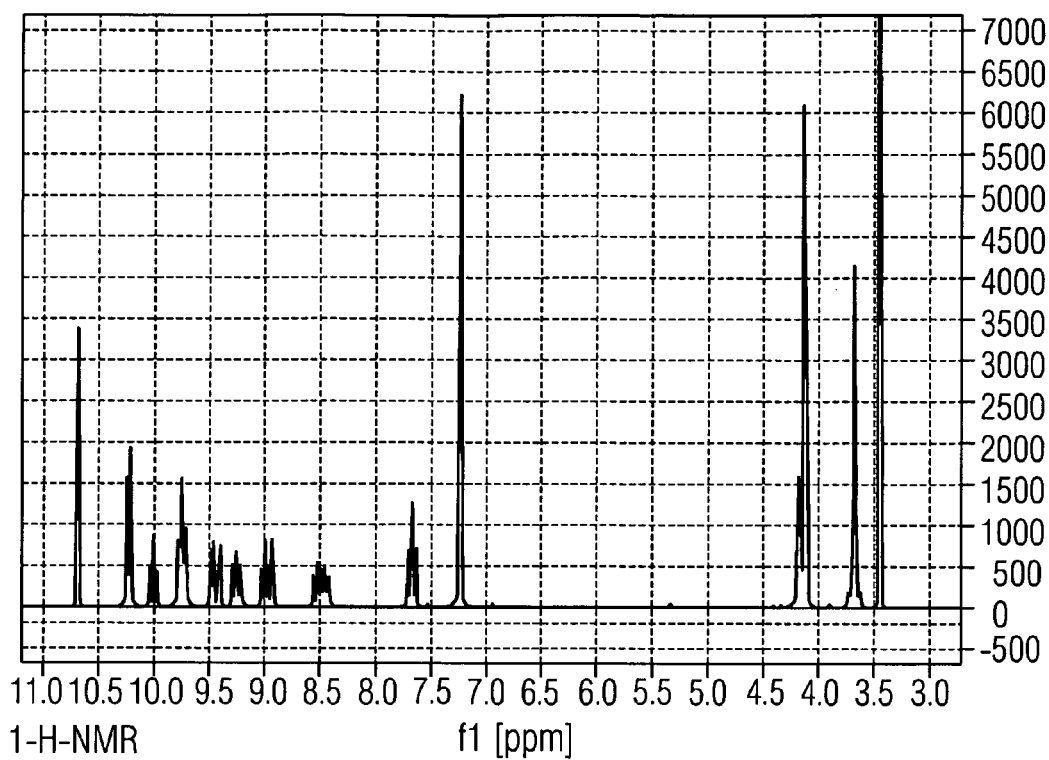
Figure 4:
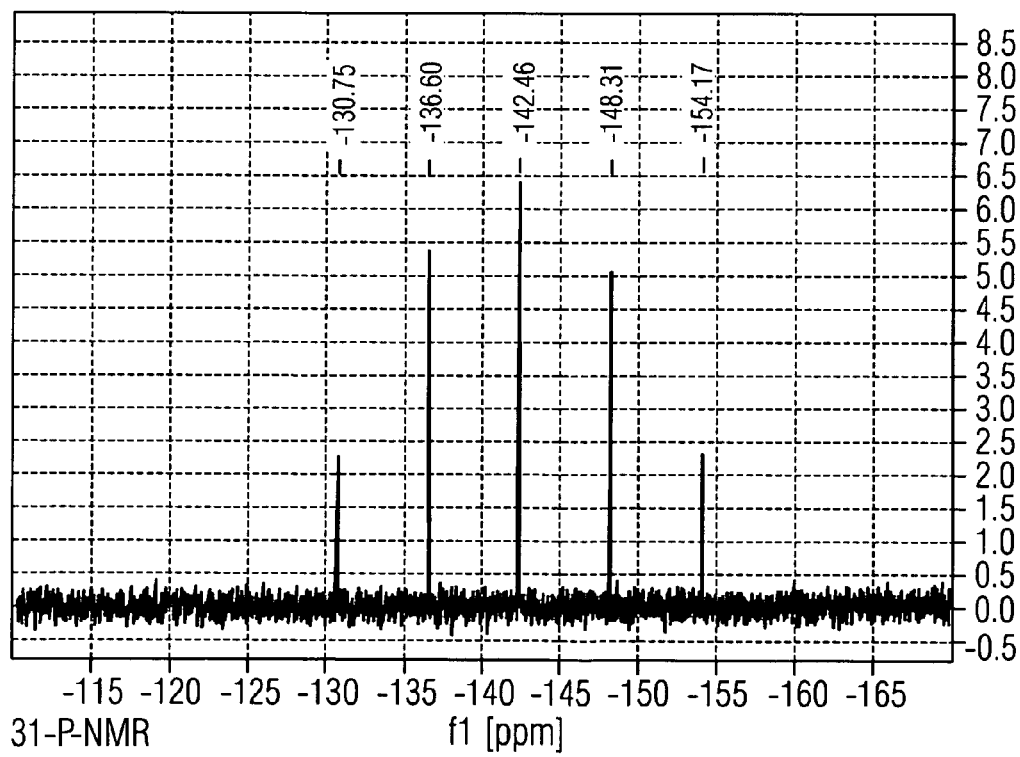
Figure 5:
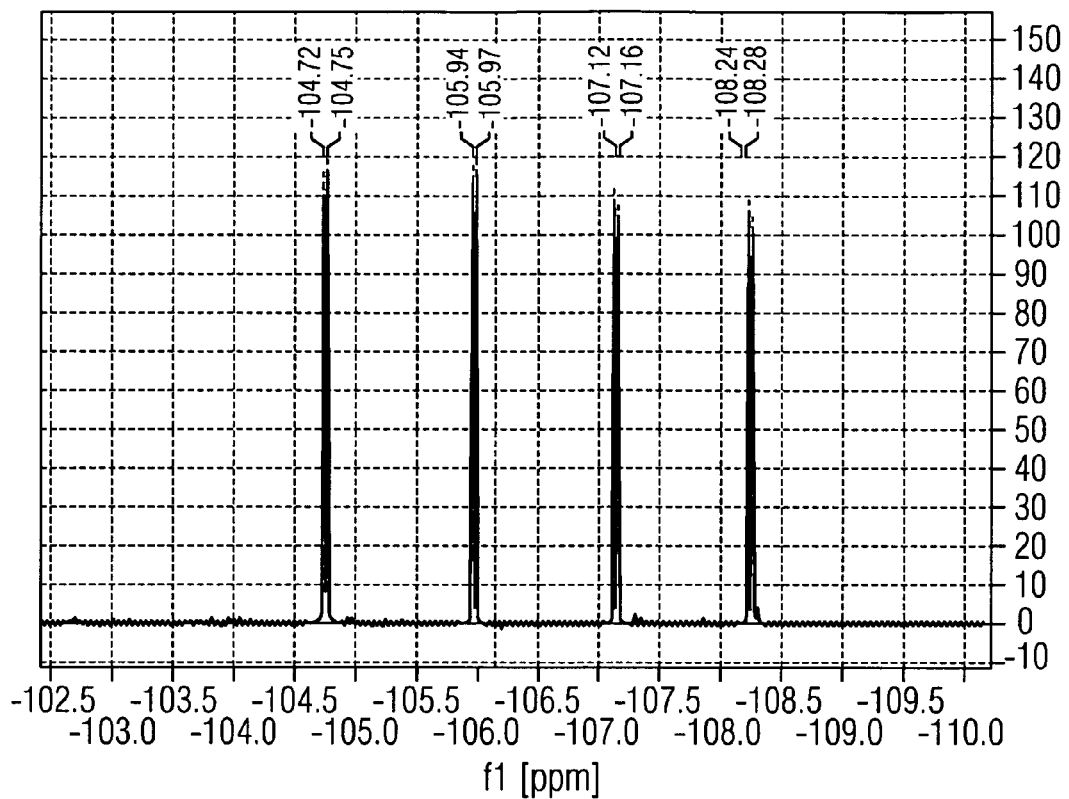

Reference will now be made in detail to the preferred embodiments of the present invention, examples of which are illustrated in the accompanying drawings, wherein like reference numerals refer to like elements throughout.

Other individual synthesis examples will now be described in detail.

Example 1

Synthesis of [F2(ppy)Ir(adamantyl triazolyl pyridine)]BF4 a) Preparation of Ligands:

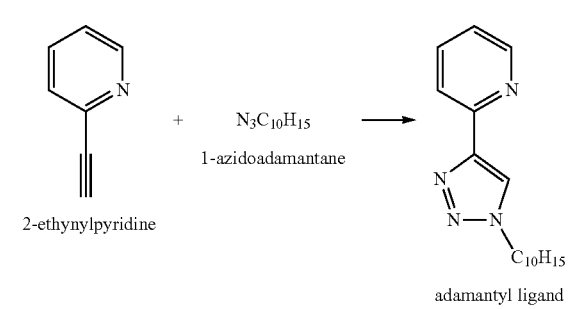

Description: 1 equivalent of an azide component and 1 equivalent of 2-ethylpyridine are mixed with a catalytic quantity of copper bromide and pentamethyldiethylene triamine (both with approx. 0.04 equivalents) in a freshly distilled oxygen-free tetrahydrofuran (6 ml). The mixture reacts exhaustively for 12 hours at room temperature in a nitrogen atmosphere. After removal of the solvent under reduced pressure, the solid matter is column chromatographically purified in hexane/ether 20/80 as the mobile phase. A white crystalline compound is obtained.

FIG. 1 shows the $^1$H proton spectrum of the compound.

$^1$H NMR (300 MHz, CD2Cl2) δ 8.54 (d, J=4.2, 1H), 8.23 (s, 1H), 8.13 (d, J=8.0, 1H), 7.77 (t, J=9.0, 1H), 7.24-7.18 (m, 1H), 2.29 (s, 9H), 1.82 (s, 6H). HRMS calculated for (C17H20N4)H 281.1761 [MH], found 281.1648.

b) Reaction of the Ligand with the Chloro-Bridged Iridium Parent Compound.

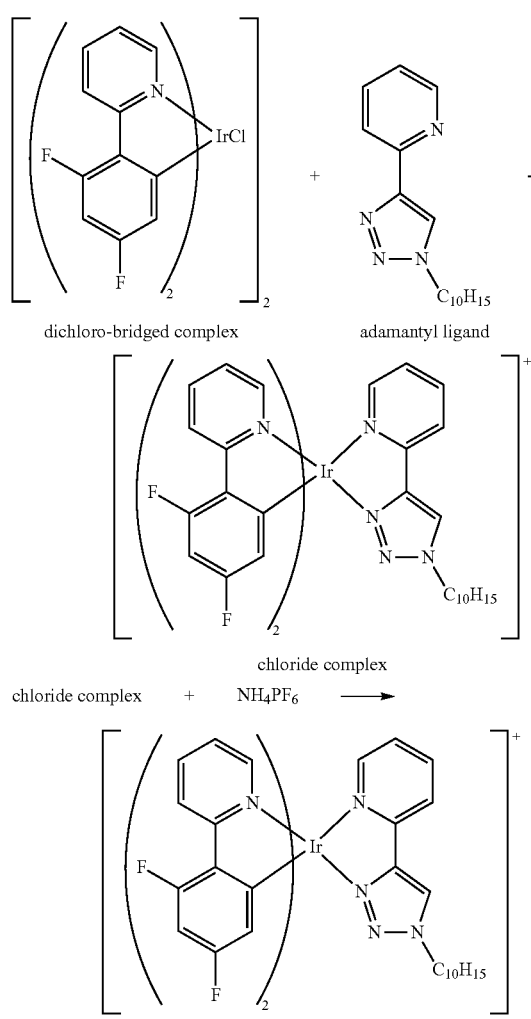

dichloro-bridged complex      adamantyl ligand chloride complex chloride complex + NH₄PF₆ ⟶

1 equivalent of the dichloro-bridged iridium complex and 2.2 equivalents of the adamantyl ligand are dissolved in 30 ml dichloromethane and 10 ml methanol. The mixture is then transferred to a 2-necked flask where it exhaustively reacts in 4 hours at 45° C. in a nitrogen atmosphere. When the mixture has cooled down to room temperature, the solvents are removed at reduced pressure and the excess ligand is chromatographically separated via a silicate powder with ethyl acetate and methanol as the mobile phase. The purified product in the form of its chloride is re-dissolved in methanol. A saturated solution of NH₄PF₆ in methanol is then added. The mixture is agitated for several hours and then concentrated at reduced pressure in order to precipitate the yellow solid which is then rinsed 3× with water (3×20 ml) and 2× with cold methanol (2×20 ml).

FIGS. 2 to 5 show the respective NMR spectra of the compound.

$^1$H NMR (300 MHz, CDCl3) δ 10.69 (s, 1H), 10.27-10.16 (m, 3H), 10.00 (t, J=6, 1H), 9.81-9.70 (m, 3H), 9.46 (d, J=6, 1H), 9.41 (d, J=6, 1H), 9.28 (t, J=6, 1H), 9.01 (t, J=9.0, 1H), 8.95 (t, J=9.0, 1H), 8.58-8.40 (m, 2H), 7.66 (t, J=9, 2H), 4.13 (s, 9H), 3.69 (s, 6H). HRMS calculated for $C_{39}H_{32}F_4IrN_6$ 853.2254 [M-PF₆], found 853.2171.

c) Conversion of the Chloride to the Tetrafluoroborate:

chloride complex + NH₄BF₄ ⟶

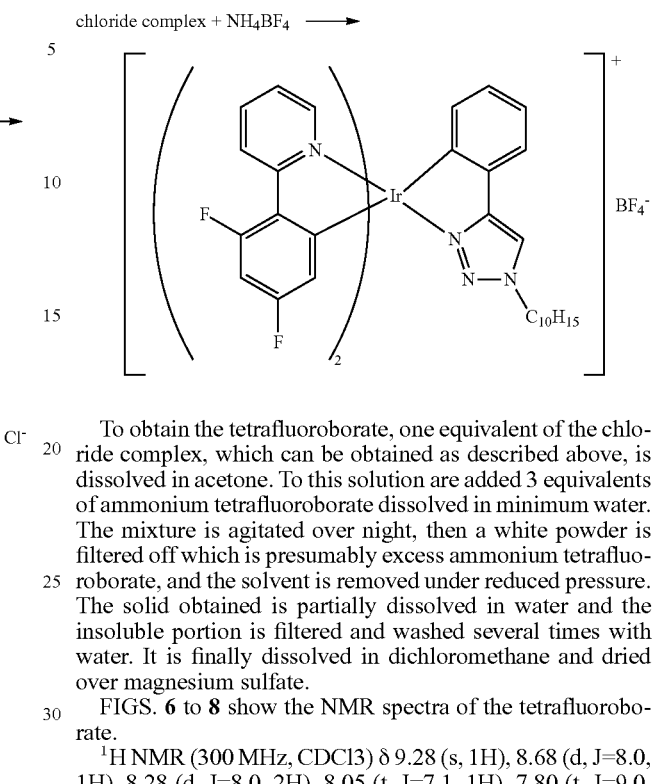

To obtain the tetrafluoroborate, one equivalent of the chloride complex, which can be obtained as described above, is dissolved in acetone. To this solution are added 3 equivalents of ammonium tetrafluoroborate dissolved in minimum water. The mixture is agitated over night, then a white powder is filtered off which is presumably excess ammonium tetrafluoroborate, and the solvent is removed under reduced pressure. The solid obtained is partially dissolved in water and the insoluble portion is filtered and washed several times with water. It is finally dissolved in dichloromethane and dried over magnesium sulfate.

Figure 6:
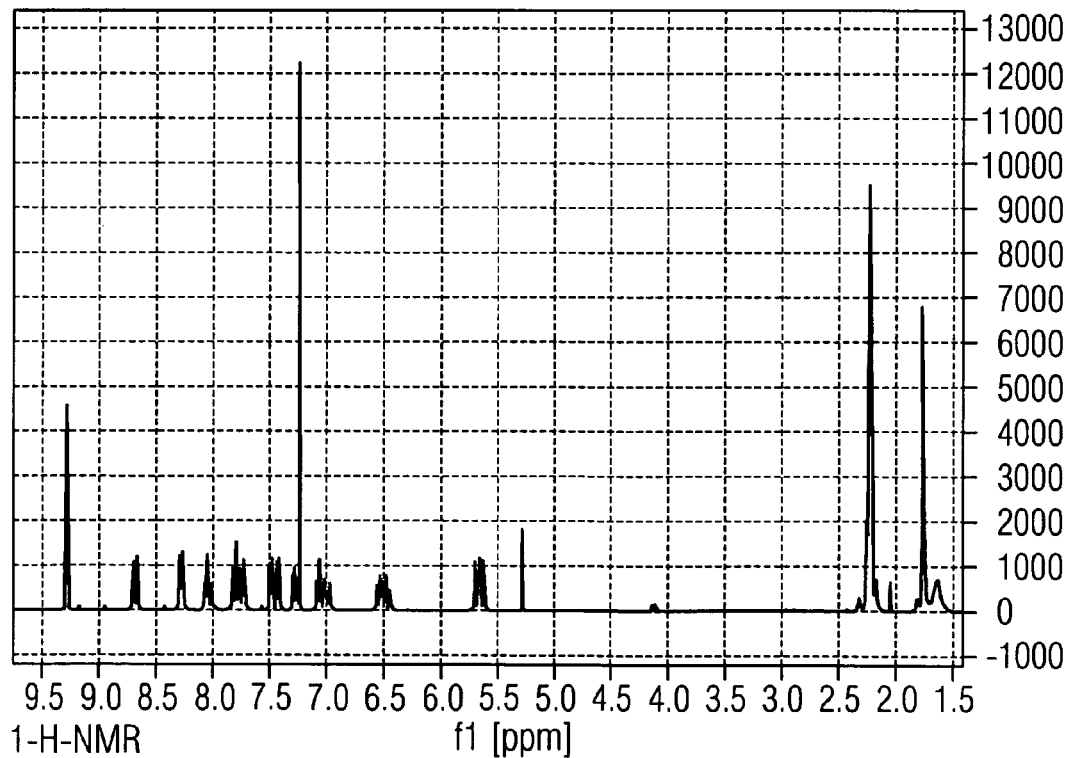
FIGS. 6 to 8 show the NMR spectra of the tetrafluoroborate.
Figure 7:
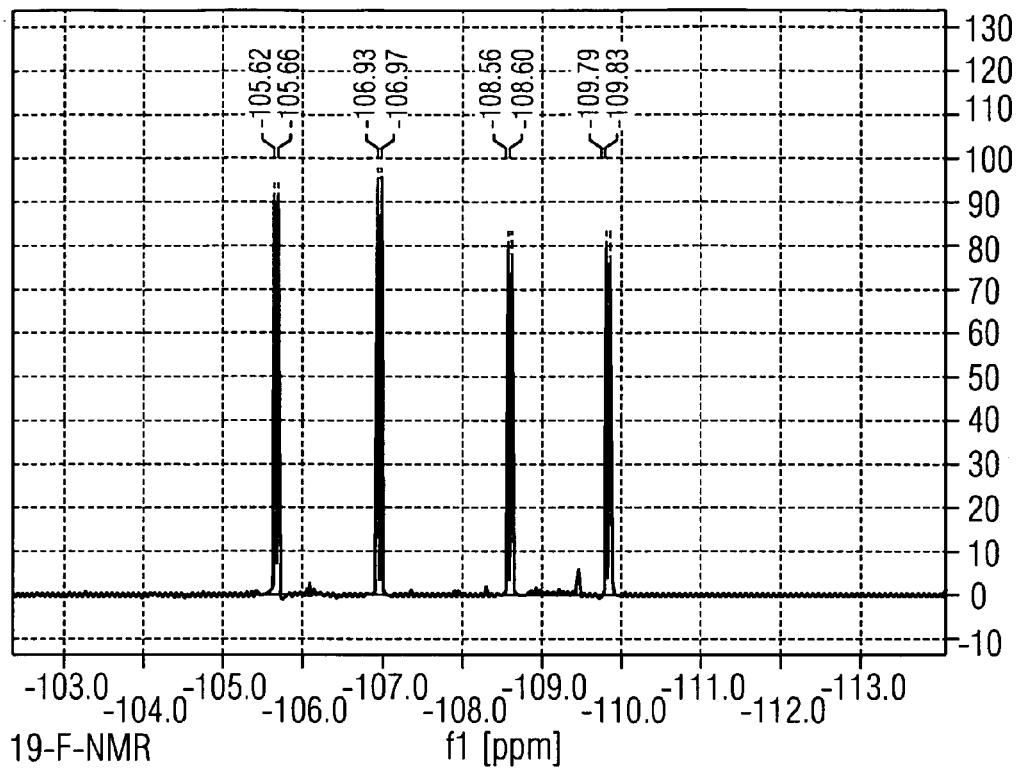
Figure 8:
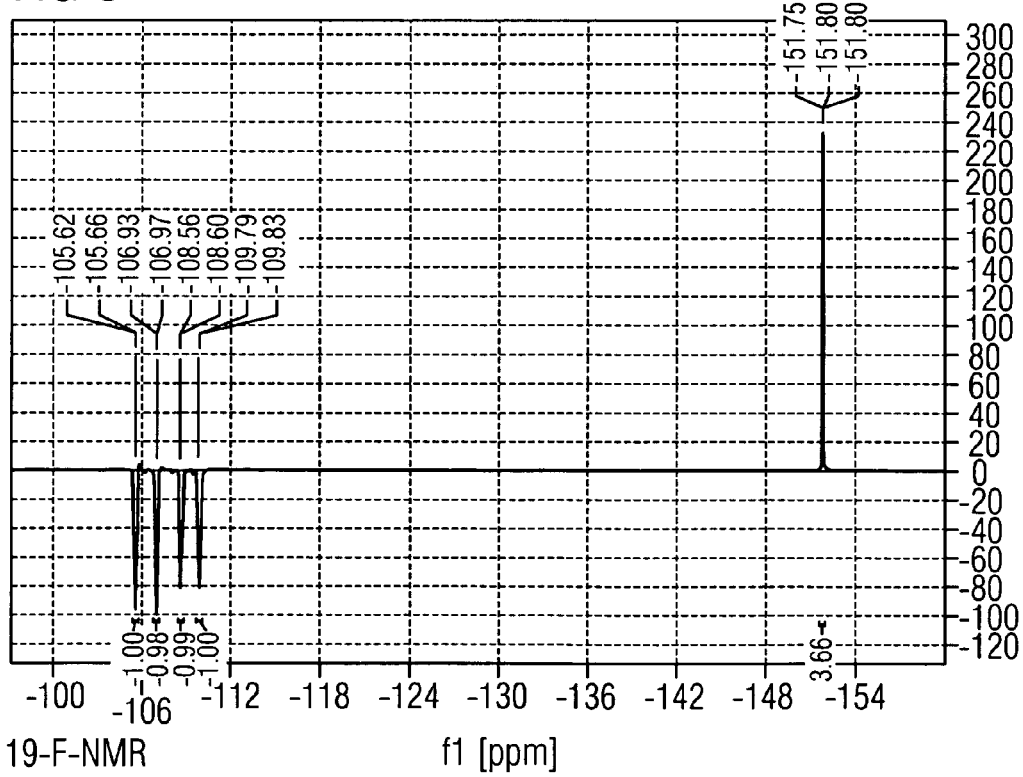

FIGS. 6 to 8 show the NMR spectra of the tetrafluoroborate.

$^1$H NMR (300 MHz, CDCl3) δ 9.28 (s, 1H), 8.68 (d, J=8.0, 1H), 8.28 (d, J=8.0, 2H), 8.05 (t, J=7.1, 1H), 7.80 (t, J=9.0, 2H), 7.73 (d, J=3.0, 1H), 7.50 (d, J=6.0, 1H), 7.44 (d, J=6.0, 1H), 7.29 (t, J=6.0, 1H), 7.08 (t, J=6.0, 1H), 7.01 (t, J=6.0, 1H), 6.59-6.44 (m, 2H), 5.72-5.60 (m, 2H), 2.19 (s, 9H), 1.72 (s, 6H). HRMS calculated for $C_{39}H_{32}F_4IrN_6$ 853.2254 [M-BF₄], found 853.2148.

Figure 9:
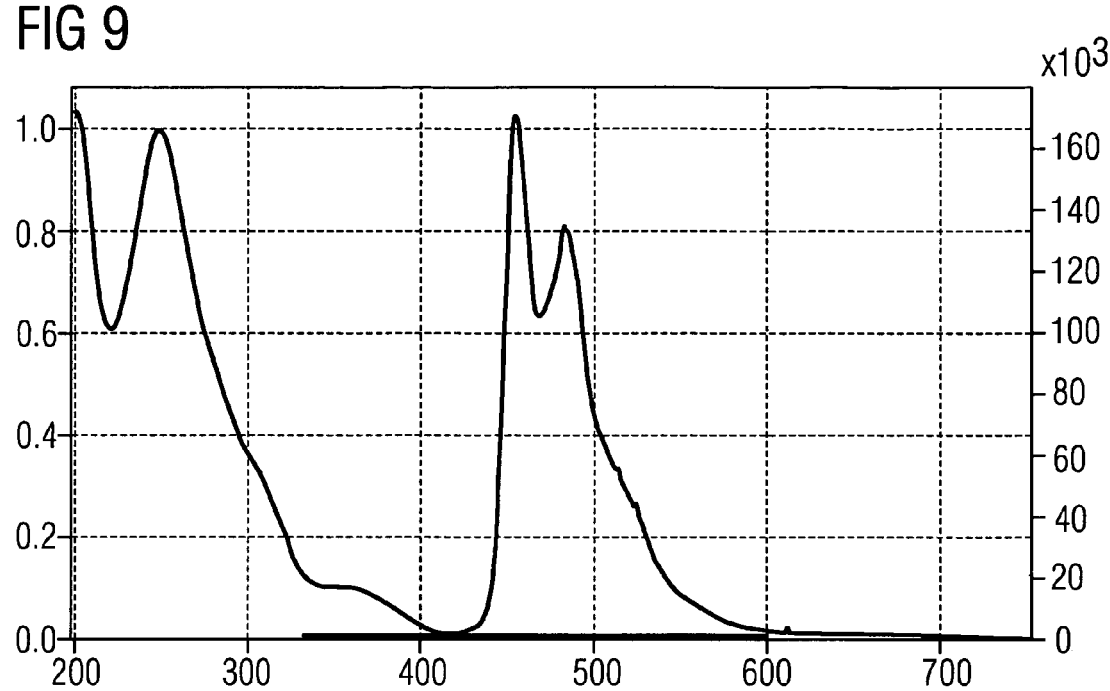
FIGS. 9 to 10 show spectra of [F2(ppy)Ir(adamantyl triazolyl pyridine)]PF6; a photoluminescence spectrum (FIG. 9) and an electroluminescence spectrum (FIG. 10).
Figure 10:
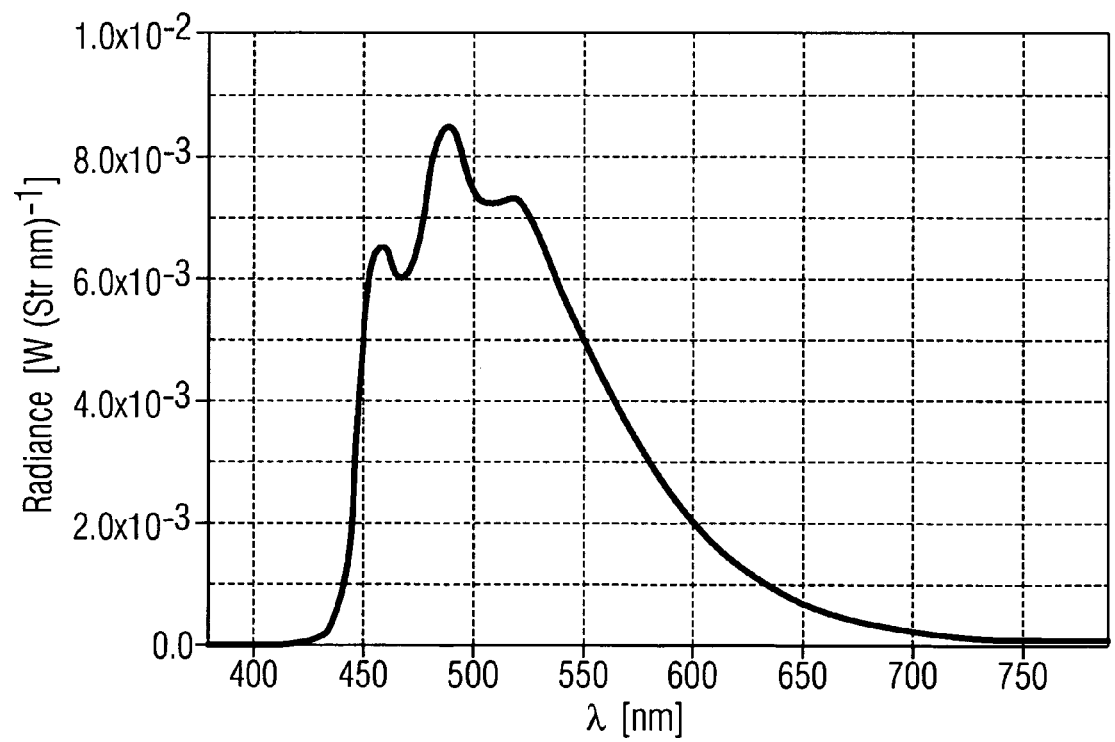

FIGS. 9 to 10 show spectra of [F2(ppy)Ir(adamantyl triazolyl pyridine)]PF6; a photoluminescence spectrum (FIG. 9) and an electroluminescence spectrum (FIG. 10).

Figure 11:
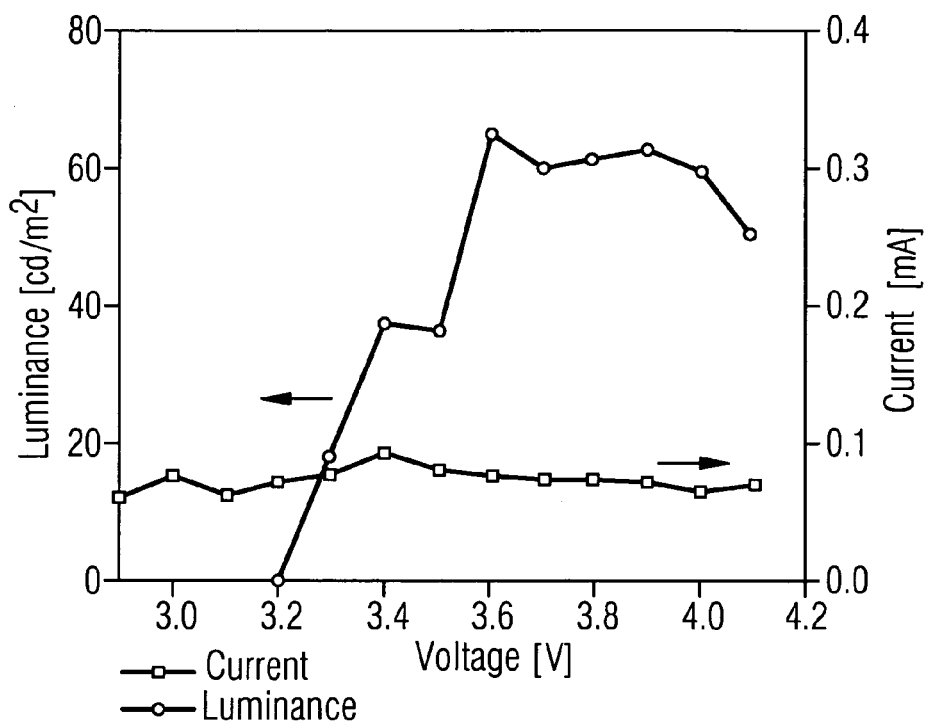
FIG. 11 shows the light-current-voltage characteristic of the compound [F2(ppy)Ir(adamantyl triazolyl pyridine)]PF6.

FIG. 11 shows the light-current-voltage characteristic of the compound [F2(ppy)Ir(adamantyl triazolyl pyridine)]PF6.

Figure 12:
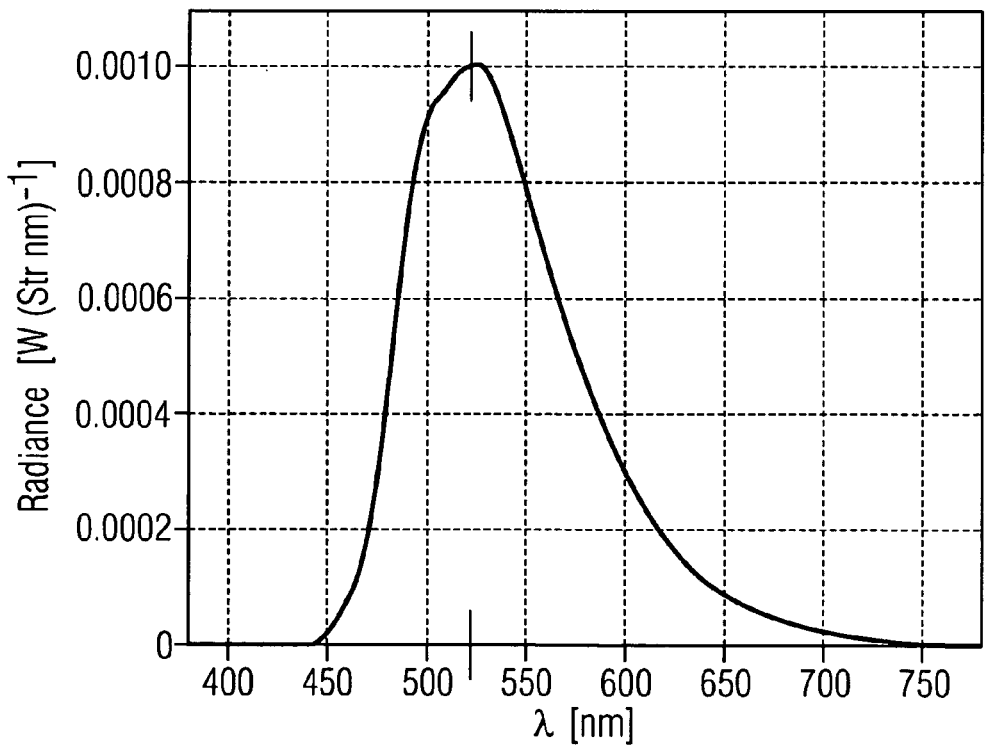
FIG. 12 shows an electroluminescence spectrum of the tetrafluoroborate compound [F2(ppy)Ir(adamantyl triazolyl pyridine)]BF4.

FIG. 12 shows an electroluminescence spectrum of the tetrafluoroborate compound [F2(ppy)Ir(adamantyl triazolyl pyridine)]BF4.

Figure 13:
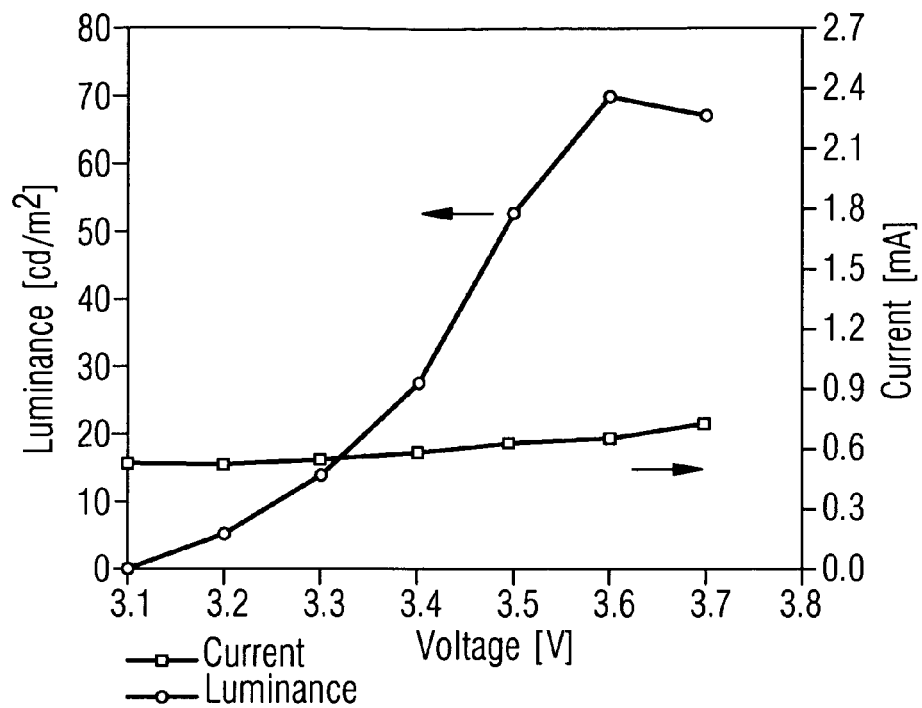
FIG. 13 shows the light-current-voltage characteristic, this time of the compound [F2(ppy)Ir(adamantyl triazolyl pyridine)]BF4.

FIG. 13 shows the light-current-voltage characteristic, this time of the compound [F2(ppy)Ir(adamantyl triazolyl pyridine)]BF4.

Figure 14:
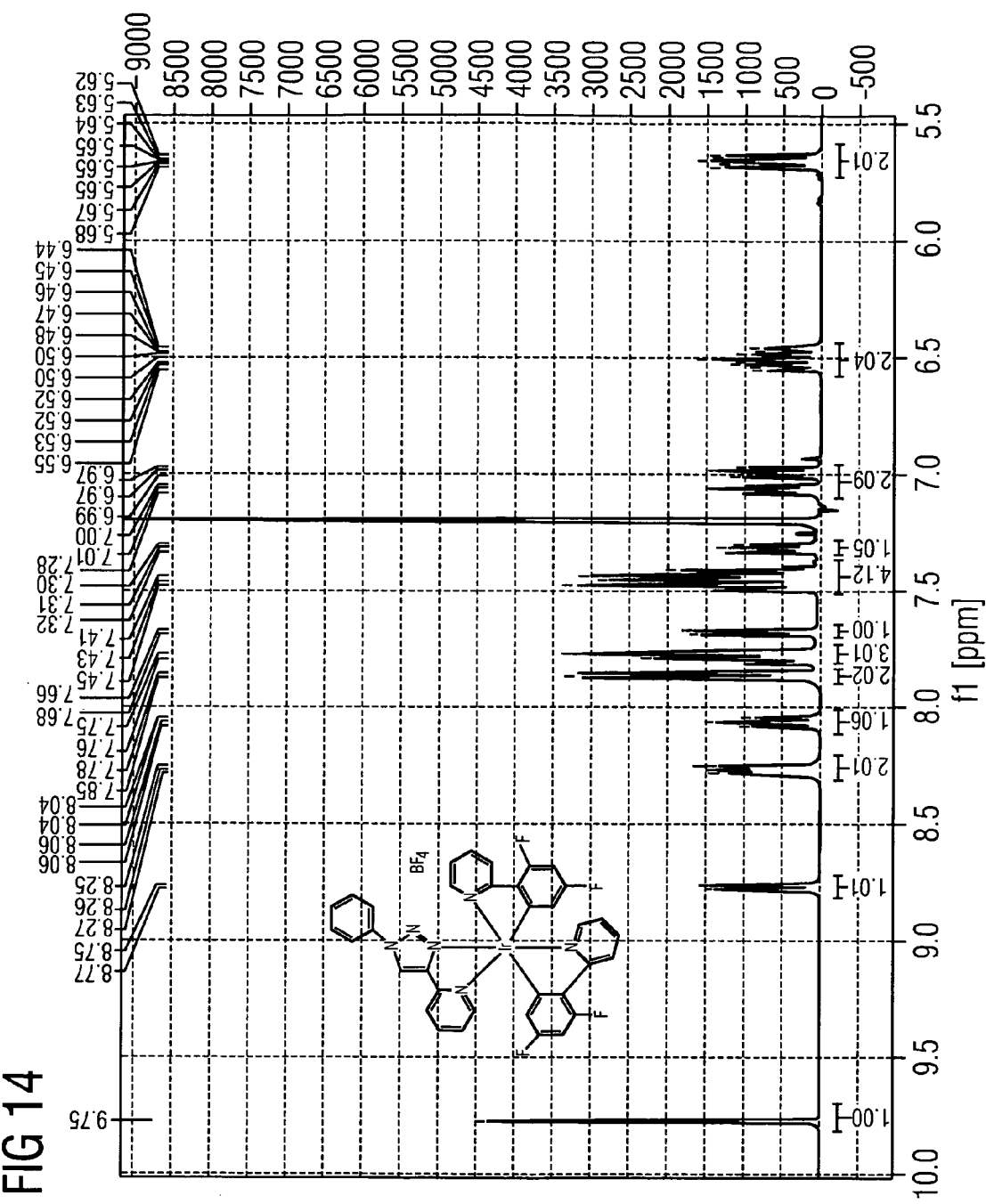
FIG. 14 shows the 1-H NMR for the compound bis(2,4-difluorophenyl-pyridyl) (4-pyridyl-1-phenyl-triazole) iridium (III) tetrafluoroborate.

FIG. 14 shows the 1-H NMR for the compound bis(2,4-difluorophenyl-pyridyl) (4-pyridyl-1-phenyl-triazole) iridium (III) tetrafluoroborate.

Table 1 shows the redox potentials of the bridged iridium (III) compounds.

| Compound | $E_{1/2}^{Red}$ (V) | $E_{1/2}^{Ox}$ (V) |
|---|---|---|
| Flu | −1.72; −2.06 | — |
| Ir-flu-Ir | −2.05[b] | 0.88 |
| FFIr-flu-IrFF | −1.96[b] | 1.21 |
| Ru-flu-Ru | −1.76; −1.94[c] | 0.93 |

[a]Scanrate 100 mV/s
[b]Irreversible.
[c]Adsorption at the electrode.

The measurements were carried out in water-free acetonitrile (for the complexes), and in THF for the ligands, (Flu) the values were measured compared to ferrocene/ferrocenium as the internal standard.

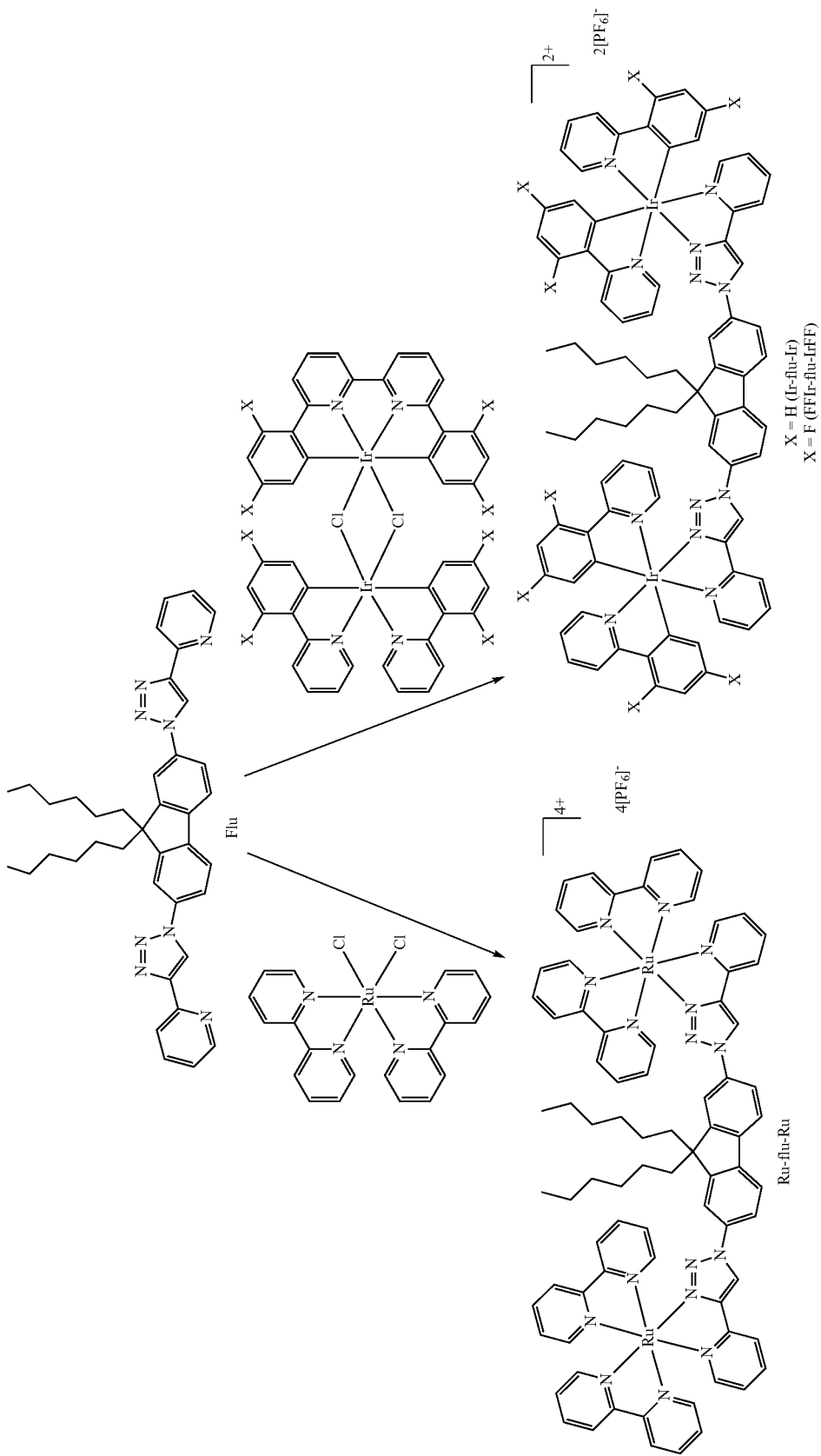

Figure 15:
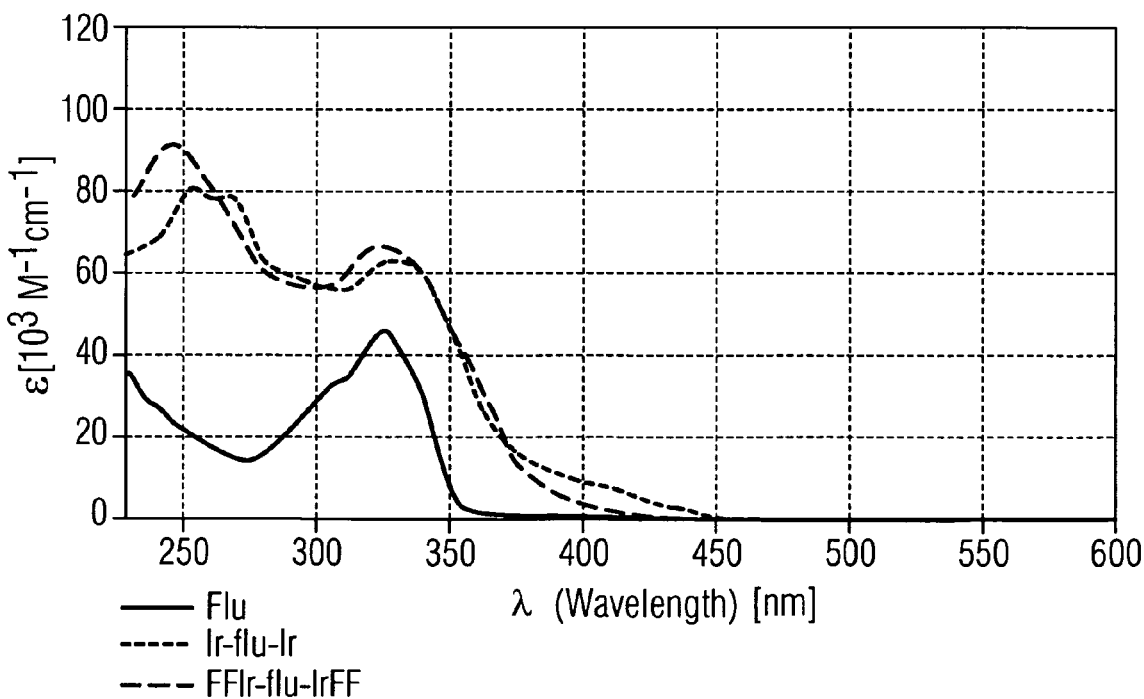
FIG. 15 shows an absorption spectrum of a bridged iridium (III) triazole compound.

FIG. 15 shows an absorption spectrum of a bridged iridium (III) triazole compound.

Figure 16:
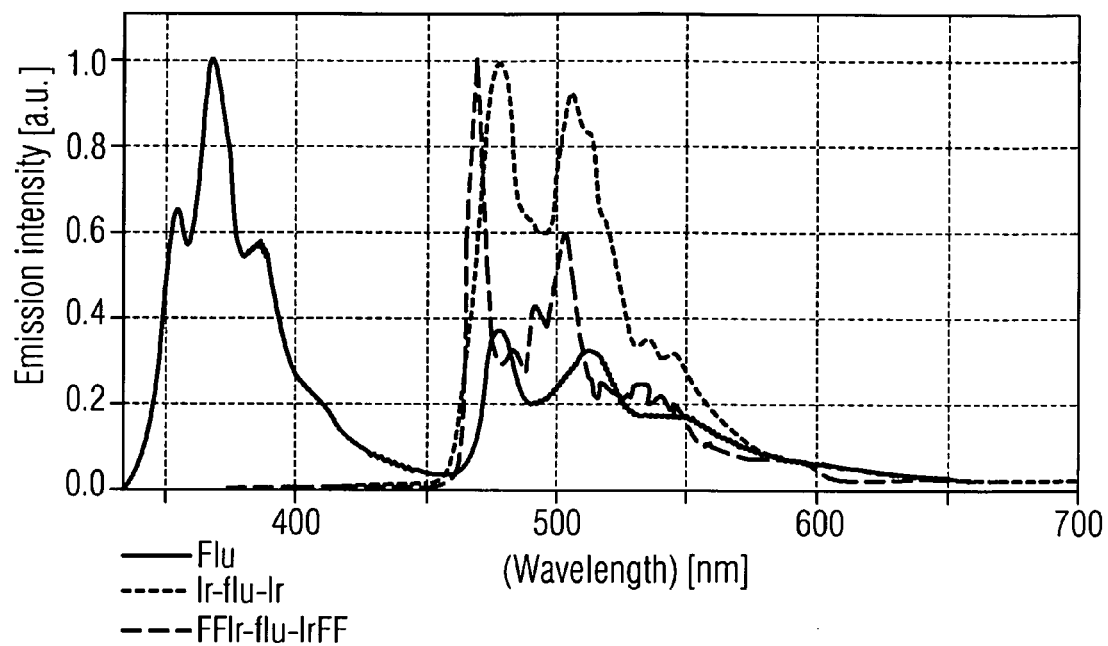
FIG. 16 shows a photoluminescence spectrum of the bridged iridium (III) compound as described above at a temperature of 77 Kelvin and FIG. 17 shows another photoluminescence spectrum of the bridged iridium (III) compound at room temperature.
Figure 17:
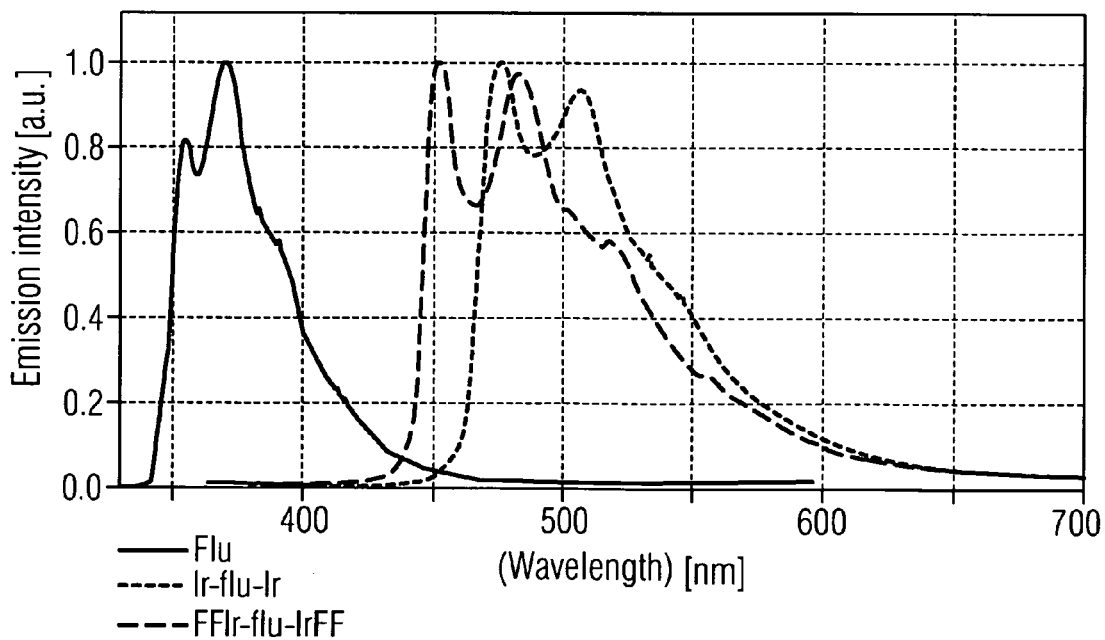

FIG. 16 shows a photoluminescence spectrum of the bridged iridium (III) compound as described above at a temperature of 77 Kelvin and FIG. 17 shows another photoluminescence spectrum of the bridged iridium (III) compound at room temperature.

Shown below are structures of two triazole ligands which are used by way of example according to the inventors' proposals, thereby producing highly efficient blue emitters.

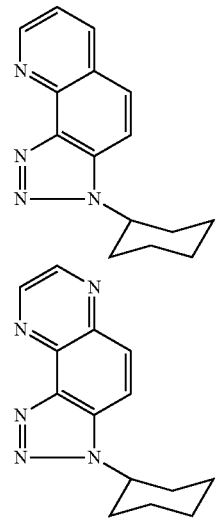

The triazole ligand system can be used to produce blue and green emitters which can be used in organic light emitting electrochemical cells (OLEECs). Some of the emitters shown here for the first time, in particular the class of iridium complex compounds presented here, are the bluest emitters that have ever existed.

The invention has been described in detail with particular reference to preferred embodiments thereof and examples, but it will be understood that variations and modifications can be effected within the spirit and scope of the invention covered by the claims which may include the phrase "at least one of A, B and C" as an alternative expression that means one or more of A, B and C may be used, contrary to the holding in *Superguide v. DIRECTV*, 69 USPQ2d 1865 (Fed. Cir. 2004).

The invention claimed is:

1. A light-emitting organic electrochemical cell comprising:
   a substrate;
   a first electrode layer on the substrate;
   at least one organic emitting layer on the first electrode layer; and
   a second electrode layer on the organic emitting layer, wherein each organic emitting layer comprises a charged phosphorescent metal complex having the structural formula:

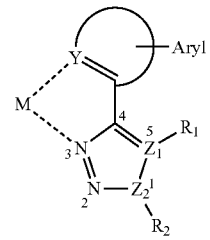

where:
M=Ir, Re, Os, Pt, Au, Hg, Ru, Rh, Pd, Ag, or Cu,
$Z_1$=C, $Z_2$=N,
Aryl=any partly or fully substituted aromatic or heteroaromatic radical which may also be fused, may form a bridge to a further compound, may be fused and/or annelated to further aromatic or heteroaromatic systems, and/or may be bonded to further cyclic compounds,
and one of (a) and (b):
  (a) Y=N and $R_1$ and $R_2$ are independently selected from the group consisting of H, alkyl radicals, alkoxy groups, amines, amides, esters, carbonates, aromatic systems, heteroaromatic systems, halogens and pseudohalogens,
  (b) Y=C and $R_1$ and $R_2$ are independently selected from the group consisting of H, alkyl radicals, alkoxy groups, amines, amides, esters, carbonates, aromatic systems, heteroaromatic systems, halogens and pseudohalogens.

2. The electrochemical cell as claimed in claim 1, wherein the metal complex has at least two metallic central atoms that are bridged.

3. The electrochemical cell as claimed in claim 1, wherein the metal complex is multinuclear and has at least two metallic central atoms M.

4. The electrochemical cell as claimed in claim 1, wherein the metal complex contains a bridging ligand, and
the at least two metallic central atoms M are linked via the bridging ligand.

5. The electrochemical cell as claimed in claim 1, wherein the phosphorescent metal complex is present in a matrix material.

6. The electrochemical cell as claimed in claim 1, wherein when a voltage is applied between the first and second electrode layers, the at least one organic emitting layer emits light with a color selected from the group consisting of green, blue-green, and blue.

7. The electrochemical cell as claimed in claim 1, wherein the substrate and the first electrode layer are transparent.

* * * * *

UNITED STATES PATENT AND TRADEMARK OFFICE
CERTIFICATE OF CORRECTION

PATENT NO. : 9,012,038 B2
APPLICATION NO. : 12/737466
DATED : April 21, 2015
INVENTOR(S) : Luisa De Cola et al.

Page 1 of 1

It is certified that error appears in the above-identified patent and that said Letters Patent is hereby corrected as shown below:

In the Claims

Column 20, Line 41, In Claim 4, delete "claim 1," and insert -- claim 3, --, therefor.

Signed and Sealed this
Eighteenth Day of August, 2015

Michelle K. Lee
*Director of the United States Patent and Trademark Office*